United States Patent
Laut

(10) Patent No.: US 8,342,362 B2
(45) Date of Patent: Jan. 1, 2013

(54) METER FOR A DEVICE FOR DISTRIBUTING A FLUID OR POWDER PRODUCT

(75) Inventor: Antoine Laut, Etrepagny (FR)

(73) Assignee: Aptar France SAS, Le Neubourg (FR)

( * ) Notice: Subject to any disclaimer, the term of this patent is extended or adjusted under 35 U.S.C. 154(b) by 1 day.

(21) Appl. No.: 13/142,767

(22) PCT Filed: Dec. 28, 2009

(86) PCT No.: PCT/FR2009/052708
§ 371 (c)(1),
(2), (4) Date: Jun. 29, 2011

(87) PCT Pub. No.: WO2010/076531
PCT Pub. Date: Jul. 8, 2010

(65) Prior Publication Data
US 2011/0266305 A1    Nov. 3, 2011

(30) Foreign Application Priority Data
Dec. 30, 2008 (FR) ........................... 08 59140

(51) Int. Cl.
*B67D 7/22* (2010.01)
(52) U.S. Cl. .................... 222/36; 128/205.23
(58) Field of Classification Search .............. 222/36, 222/47–49; 128/205.23, 203.15, 203.12, 128/200.11–200.24; 116/309, 311–318
See application file for complete search history.

(56) References Cited

U.S. PATENT DOCUMENTS

| | | | | |
|---|---|---|---|---|
| 6,659,307 B1* | 12/2003 | Stradella | | 222/23 |
| 7,322,352 B2* | 1/2008 | Minshull et al. | | 128/203.15 |
| 7,387,122 B2* | 6/2008 | Nishibayashi et al. | | 128/203.15 |
| 7,766,188 B2* | 8/2010 | Pocock et al. | | 222/36 |
| 7,882,982 B2* | 2/2011 | Stradella et al. | | 222/38 |
| 8,113,199 B2* | 2/2012 | Augustyn et al. | | 128/205.23 |
| 8,186,343 B2* | 5/2012 | Stradella et al. | | 128/200.14 |
| 8,245,906 B2* | 8/2012 | Crosby et al. | | 235/91 R |
| 2004/0255935 A1* | 12/2004 | Bruna | | 128/200.23 |

FOREIGN PATENT DOCUMENTS

| | | |
|---|---|---|
| WO | 2005/114563 A1 | 12/2005 |
| WO | 2007/077450 A2 | 7/2007 |
| WO | 2007/104964 A1 | 9/2007 |

* cited by examiner

*Primary Examiner* — Lien Ngo
(74) *Attorney, Agent, or Firm* — Sughrue Mion, PLLC

(57) ABSTRACT

A dose counter for counting the number of doses of fluid or powder that have been dispensed or that remain to be dispensed from a fluid dispenser device, said counter including a first rotary counter element (110) forming a units wheel, and a second rotary counter element (120) forming a tens wheel, said first and second counter elements co-operating with each other to define and to display, in a viewing window, said number of doses, said first counter element co-operating with an actuator member (130) that is adapted to cause said first counter element to turn each time said actuator member is actuated, said counter including an intermediate rotary element (140) that is adapted to cause said second counter element to turn on every tenth actuation of said actuator member, said first and second counter elements turning about a common first pivot pin (161), and said intermediate element turning about a second pivot pin (162) that is offset and parallel to said first pivot pin.

23 Claims, 4 Drawing Sheets

METER FOR A DEVICE FOR DISTRIBUTING A FLUID OR POWDER PRODUCT

CROSS REFERENCE TO RELATED APPLICATIONS

This application is a National Stage of International Application No. PCT/FR2009/052708 filed Dec. 28, 2009, claiming priority based on French Patent Application No. 08 59140, filed Dec. 30, 2008, the contents of all of which are incorporated herein by reference in their entirety.

The present invention relates to a counter, and more particularly to a dose counter, for indicating to the user the number of doses that have been dispensed or that remain to be dispensed from a fluid or powder dispenser device.

The use of counters or of indicators is well known in the field of fluid dispensers, in particular in the field of pharmaceuticals. In particular, such counters or indicators are used with dispenser devices of the metered dose inhaler (MDI) type, in which a reservoir containing fluid and a propellant gas is movably mounted in a body, movement of said reservoir actuating a metering valve mounted on said reservoir, so as to dispense a dose of fluid. A first family of counters envisages fastening the counter on the bottom of the reservoir, projecting out from the body, and on which the user presses in order to dispense a dose. However, that type of counter presents the drawback of interfering with the actuation of the dispenser device, with it being necessary for the user to press on the counter in order to actuate the device. In the event of poorly controlled or partial actuation, problems of over- and/or under-counting and/or of incomplete or faulty dispensing may thus occur. A second family of counters comprises counters that are disposed inside the body, being fastened either to the body or to the movable reservoir in said body. In particular, that type of counter presents the drawback of a complex mounting, and requires substantial modifications to the various component parts of the dispenser device. The assembly problem occurs in particular when assembly is performed by the manufacturer of the pharmaceutical, as opposed to by the manufacturer of the dispenser device, with that requiring the manufacturer of the pharmaceutical to install complex assembly machines in its own factory. A third family of counters envisages arranging the counter on an outside face of the body, a projection of said counter passing through an opening in the body, so as to co-operate with the reservoir or a portion that is secured to said reservoir. That type of counter also generally requires substantial modification to the body in order to receive the counter. In addition, the presence of a counter on the outside main face of the body substantially modifies the external appearance of the device, in particular because of the thickness of said counter, and that may also have a negative effect on the handling of the device. In addition, the counters used on dispenser devices for dispensing fluids, in particular pharmaceuticals, need to comply with several constraints. Thus, in order to avoid any risk of under-counting, it is generally required that the counter is actuated at the very beginning of the actuation stroke of the valve or the pump, so as to avoid partial actuation, causing a partial or complete dose to be dispensed without any dose being counted by the counter. In this situation, a problem that occurs is that the actuation stroke is generally very short, and that the manufacturing tolerances of the device tend to reduce even further the distance available to perform the actuation in effective manner. The use of a complex mechanism is generally required in order to provide counting that is functional and safe. In general, assembling counters, in particular counters including a plurality of rotary elements that are interleaved in one another, is found to be complex and thus not only costly, but also a source of malfunctions. Documents WO 2007/104964, WO 2007/077450, and WO 2005/114563 describe prior-art devices.

An object of the present invention is to provide a counter, more particularly a dose counter, for a fluid or powder dispenser device, that does not reproduce the above-mentioned drawbacks.

In particular, an object of the present invention is to provide such a counter that presents minimum thickness.

Another object of the present invention is to provide such a counter that can be pre-assembled prior to being delivered to the manufacturer of the pharmaceutical, said manufacturer thus needing only to perform a single step of mounting the counter on the body of the dispenser device, without any complex assembly of the component parts of said counter.

Another object of the present invention is to provide such a counter that guarantees actuation of the counter independently of the length of the actuation stroke of the pump or of the valve used in the device.

Another object of the present invention is to provide such a counter that is simpler and thus less costly to manufacture and to assemble, and that is more reliable in operation.

The present invention thus provides a dose counter for counting the number of doses of fluid or powder that have been dispensed or that remain to be dispensed from a fluid dispenser device, said counter including a first rotary counter element forming a units wheel, and a second rotary counter element forming a tens wheel, said first and second counter elements co-operating with each other to define and to display, in a viewing window, said number of doses, said first counter element co-operating with an actuator member that is adapted to cause said first counter element to turn each time said actuator member is actuated, said counter including an intermediate rotary element that is adapted to cause said second counter element to turn on every tenth actuation of said actuator member, said first and second counter elements turning about a common first pivot pin, and said intermediate element turning about a second pivot pin that is offset and parallel to said first pivot pin.

Advantageously, said first counter element includes: a first peripheral set of teeth, which set, on each actuation, co-operates with at least one actuator tab of the actuator member; and a second peripheral set of teeth, which set, on each actuation, co-operates with said intermediate element.

Advantageously, said first set of teeth is radially inside the second set of teeth, the teeth of the first set of teeth being oriented axially, and the teeth of the second set of teeth being oriented radially outwards.

Advantageously, said first counter element is substantially in the shape of a disk provided with a central through opening that is adapted to be engaged around its pivot pin, the top face of said disk including a first radially-outer peripheral edge portion that receives counter indices, such as one or more series of numbers from 0 to 9, in particular three series of numbers from 0 to 9, distributed over said periphery, and the bottom face of said disk including said first and second peripheral sets of teeth.

Advantageously, the top face of said first counter element includes a central portion that surrounds the central opening and that is extended radially outwards by an intermediate portion that is raised axially relative to said central portion, said intermediate portion being extended radially outwards by said first peripheral edge portion that is raised axially relative to said intermediate portion.

Advantageously, said second counter element includes a third peripheral set of teeth, which set, on every tenth actuation of the actuator member, co-operates with said intermediate element.

Advantageously, said second counter element is substantially in the shape of a disk provided with a central orifice, in particular a blind orifice, that is adapted to be engaged around its pivot pin, the top face of said disk including a second radially-outer peripheral edge portion that receives counter indices, such as numbers from 00 to 20, distributed over said periphery, the top face of said disk also including said third peripheral set of teeth, disposed radially inside said second outer peripheral edge portion, said third peripheral set of teeth being raised axially relative to said second outer peripheral edge portion.

Advantageously, after assembling the first and second counter elements around their common pivot pin, said second outer peripheral edge portion of said second counter element is disposed radially inside, and substantially in contact with, said first outer peripheral edge portion of said first counter element, the top surfaces of said first and second peripheral edge portions being substantially in alignment, so as to form a display zone.

Advantageously, said intermediate element includes a fourth peripheral set of teeth, which set, on each actuation of the actuator member, co-operates with a second peripheral set of teeth of said first counter element.

Advantageously, said intermediate element includes at least one radial projection that, on every tenth actuation of the actuator member, co-operates with a third peripheral set of teeth of the second counter element.

Advantageously, said at least one radial projection is formed on a radial rod portion of said intermediate element.

Advantageously, said intermediate element includes a central axial hollow sleeve, in particular a blind hollow sleeve, that defines a central orifice that is adapted to be engaged around its pivot pin, said fourth set of teeth and said radial rod portion being offset relative to each other along said sleeve, defining between them a gap for receiving a first outer peripheral edge portion of the first counter element, and a second outer peripheral edge portion of the second counter element.

Advantageously, said radial rod portion comprises two diametrally-opposite radially-outer projections that are interconnected by a curved rod zone having side edges that are in the shape of circular arcs facing in substantially opposite directions, such that in an appropriate orientation, the first and second counter elements may be assembled on their common pivot pin, after the intermediate element has been assembled on its own pivot pin.

Advantageously, the counter includes a base body and a lid, said base body incorporating the two pivot pins and an opening, and said lid incorporating a viewing window.

Advantageously, said counter may be pre-assembled so as to form a counter unit, said counter unit including fastener means for fastening to a body of a fluid dispenser device.

Advantageously, said actuator member is assembled in said base body, said actuator member including an actuator element that is movable in translation in said opening, and two flexible tabs that are movable in translation, a first flexible tab co-operating with said first set of teeth of the first counter element so as to cause said first counter element to turn in a counting direction each time the actuator element is moved from a rest position to an actuated position, and a second flexible tab co-operating with said first set of teeth of said first counter element so as to cause said first counter element to turn in the same counting direction when the actuator element returns from its actuated position to its rest position.

Advantageously, on each actuation, the first flexible tab pushes a respective first tooth of the first set of teeth of the first counter element, and the second flexible tab pulls on a respective second tooth of the first set of teeth of said first counter element.

Advantageously, the first and second teeth of the first set of teeth are substantially diametrally opposite in the first set of teeth.

Advantageously, the actuator member includes an elongate opening that is engaged around a projection of said base body, the co-operation between said projection and the edges of said elongate opening, while the actuator member is being actuated, defining the limits of the axial movement of said flexible tabs.

Advantageously, the actuator member includes an elastically-deformable portion that supports the actuator element, such that said actuator element is movable in translation over a greater distance than the flexible tabs.

Advantageously, said base body includes two shoulders that co-operate with two resilient means of the actuator member, said resilient means forming a return spring for the actuator member.

Advantageously, said lid includes a flexible tab that co-operates with a third set of teeth of said second counter element, so as to prevent said second counter element from turning while the actuator member is being actuated, the intermediate element not co-operating with said second counter element, said flexible tab deforming resiliently so as to make it possible for said second counter element to turn when said intermediate element co-operates with said second counter element, on every tenth actuation of said actuator member.

The present invention also provides a fluid or powder dispenser device comprising a reservoir, a dispenser member, such as a metering valve, that is mounted on said reservoir, and a body incorporating a dispenser orifice, said reservoir being movable in said body so as to dispense the fluid or powder, said dispenser device including a counter as described above.

Advantageously, said counter is fastened on a face of the body, said device being actuated by the user pressing axially on the reservoir, and said counter being actuated by said axial movement of said reservoir that co-operates with said actuator element of the actuator member.

The present invention also provides a method of assembling a counter, said method comprising the steps of: providing a base body that is provided with two parallel projections and with an opening; assembling an actuator member in said base body, said actuator member including an actuator element that extends out from said base body through said opening of the base body; assembling an intermediate rotary element on a first of said two projections of said base body; assembling a first rotary counter element on a second of said two projections of said base body; assembling a second rotary counter element on said second projection of said base body; and assembling a lid on said base body, so as to form a pre-assembled counter unit.

These characteristics and advantages and others of the present invention appear more clearly from the following detailed description, given by way of non-limiting example, and with reference to the accompanying drawings, in which.

Figure 1:
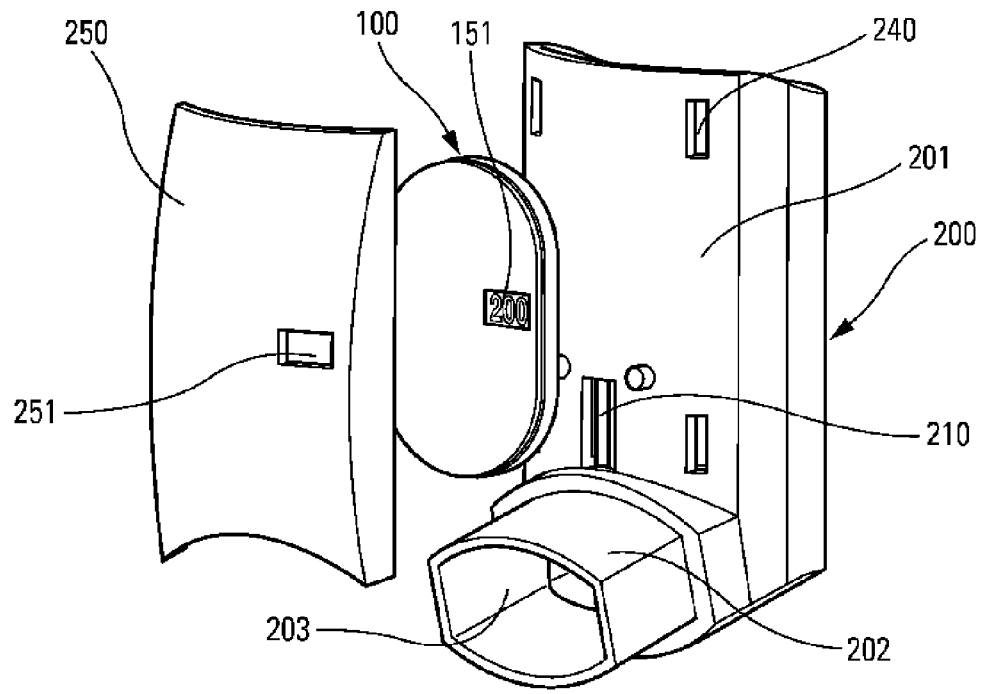
FIG. 1 is an exploded perspective view of a dispenser device including, on its front main face, a counter in a particular embodiment of the present invention.
Figure 2A:
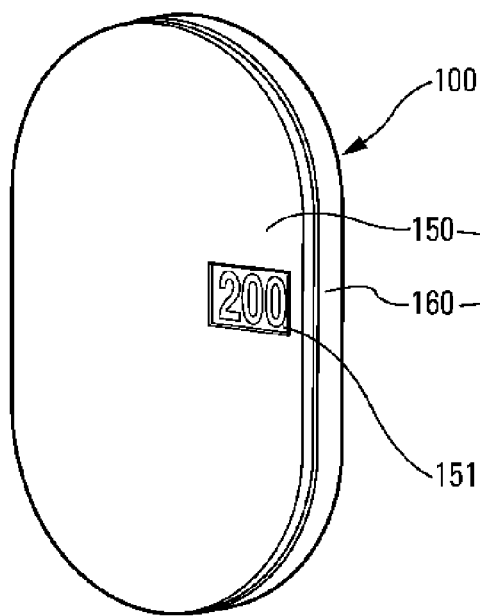
FIGS. 2a and 2b are two diagrammatic perspective views of the pre-assembled counter of FIG. 1, in front and rear views respectively.
Figure 2B:
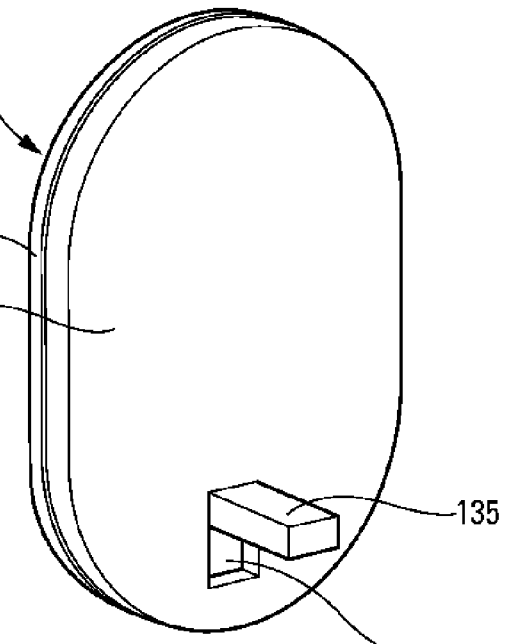

FIG. 1 shows a dispenser device of the MDI 200 type, including, on its front main face, a dose counter 100 that corresponds to a particular embodiment of the present invention. The device includes a body 201 that is provided with a mouthpiece 202 that defines a dispenser orifice 203. A reservoir (not shown) is assembled in said body 201, said reservoir including a metering valve that is mounted on its opening. Inside said body 201, the metering valve co-operates with an expulsion channel that leads into the mouthpiece 202. When the user presses on the bottom of the reservoir, said reservoir slides axially inside the body 201, causing the valve to be actuated and a dose of fluid to be expelled. The operation of such an MDI-type device is well known to the person skilled in the art, and is therefore not described more fully below. The counter 100 may be interposed between the front main face of said body 201 and a covering member 250 that includes a window 251, and that may serve to fasten the counter 100 on the body. Naturally, this embodiment is only an example, and, by way of example, the counter could be fastened directly to the body 201, independently of the presence of a covering member. The counter includes an actuator element 135 (not visible in FIG. 1, but clearly shown in FIG. 2b) that projects out from said counter, and that is adapted to penetrate inside the body 201 through an opening 210 that is provided for this purpose, so as to co-operate with the reservoir or with a portion that is secured to said reservoir. In this way, each time the dispenser device is actuated, the axial movement of the reservoir in the body 201 causes the actuator element 135 to move axially.

The counter of the invention includes: two rotary counter elements, namely a first rotary counter element 110 and a second rotary counter element 120; an actuator member 130; and an intermediate rotary element 140. The actuator member 130 that includes the actuator element 135, is for transforming an axial movement of a portion of the dispenser device 200, generally the reservoir, into a turning movement of the first counter element 110.

In a preferred variant embodiment shown in FIG. 1, the counter is disposed on a face of the body 201 of the dispenser device 200, and the actuator member 130 thus transforms an axial movement of the reservoir into a turning movement of the first counter element 110. In this configuration, the three rotary elements 110, 120, 140 of the counter turn about pivot pins 161, 162 that are substantially perpendicular to the axial movement. Advantageously, the actuation cycle of the counter may start at the very beginning of the stroke of the reservoir, such that the counter is actuated before any fluid is dispensed.

The first rotary counter element 110 forms the units wheel, and the second rotary counter element 120 forms the tens wheel, said first and second counter elements co-operating with each other to define and to display, in a viewing window 151, the number of doses of fluid that have been dispensed or that remain to be dispensed from said reservoir. Preferably, this number is formed by a display zone in which the number is displayed horizontally when the dispenser device 200 is in its normal working position, shown in FIG. 1, in which the body 201 is substantially vertical with the mouthpiece 202 disposed at the bottom. Said first counter element 110 co-operates with the actuator member 130 that is adapted to cause said first counter element 110 to turn each time said actuator member is actuated. The intermediate rotary element 140 is adapted to cause said second counter element 120 to turn on every tenth actuation of said actuator member 130, and thus on every tenth turn of said first counter element 110. In the invention, said first and second counter elements 110, 120 turn about a common first pivot pin 161, and said intermediate element 140 turns about a second pivot pin 162 that is offset and parallel to said first pivot pin 161.

Figure 3:
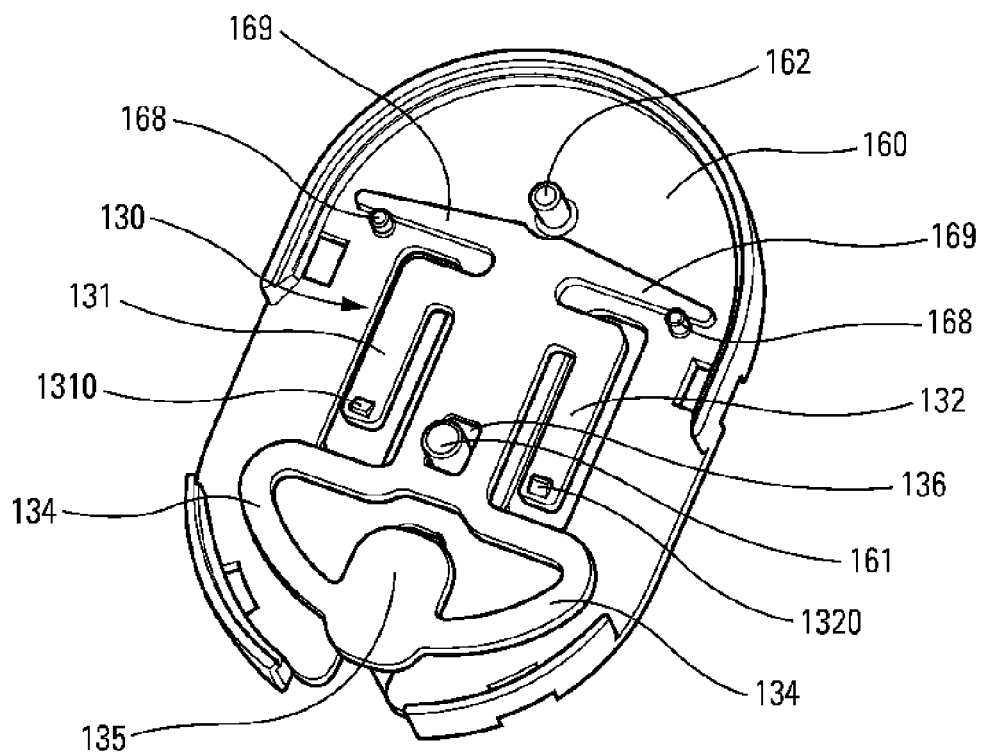
FIG. 3 is a diagrammatic perspective view of the actuator member in an advantageous embodiment of the invention.
Figure 5:
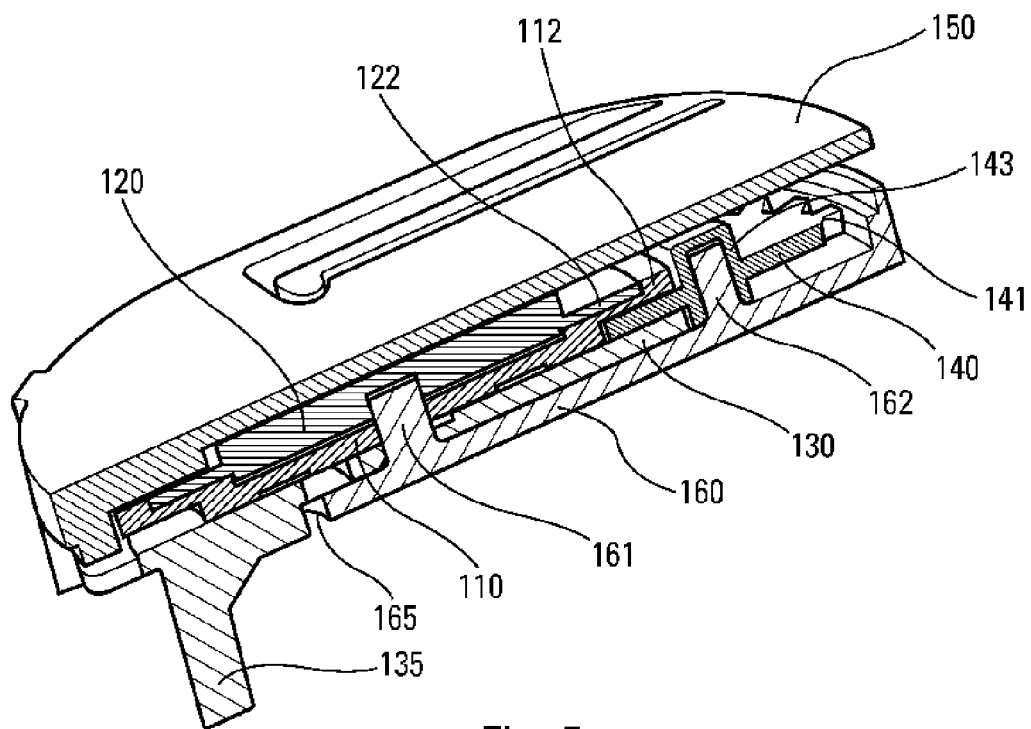
FIG. 5 is a diagrammatic section view in perspective of the counter, in an advantageous embodiment.
Figure 6:
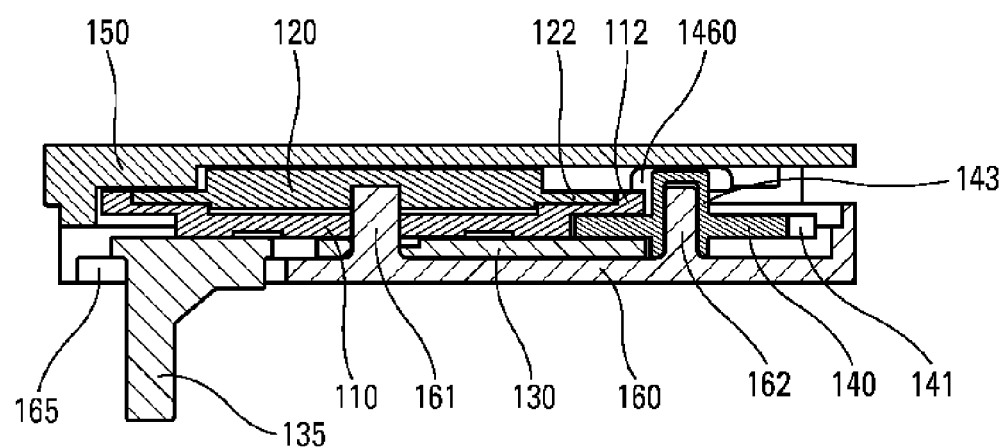
FIG. 6 is a diagrammatic cross-section view of the FIG. 5 counter.

As shown in FIGS. 3, 5, and 6, the counter preferably includes a base body 160 and a lid 150. Said base body forms the pivot pins 161 and 162, and includes an opening 165 through which the actuator element 135 is able to pass. The lid 150 includes a viewing window 151 enabling the user to see the display zone that is formed jointly by said radially-outer edge portions 112, 122. Thus, said counter may advantageously be pre-assembled so as to form a counter unit, said counter unit possibly including fastener means for fastening to the body 201 of the fluid dispenser device 200.

Figure 7A:
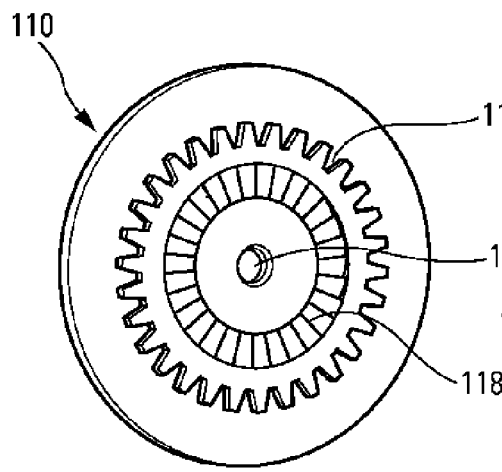
FIGS. 7a and 7b are diagrammatic rear and front views respectively of the first rotary counter element, in an advantageous variant embodiment.
Figure 7B:
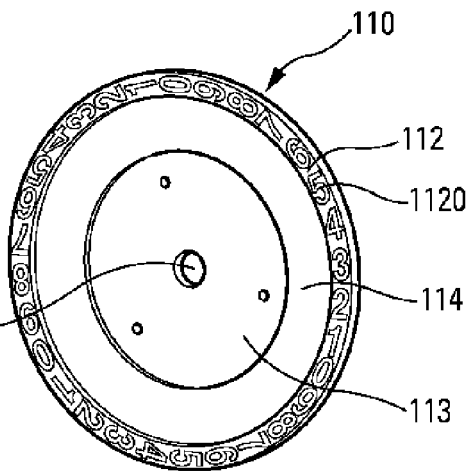

As shown in FIGS. 7a and 7b, said first counter element 110 may include a first peripheral set of teeth 118, which set, on each actuation, co-operates with at least one, preferably two flexible actuator tabs 131, 132 of the actuator member 130. A second peripheral set of teeth 111 is for co-operating, on each actuation, with the intermediate element 140. Advantageously, said first counter element 110 is substantially disk shaped, being provided with a central through opening 115 that is adapted to be engaged around its pivot pin 161. The top face of said disk includes a first radially-outer peripheral edge portion 112 that receives counter indices 1120, such as one or more series of numbers from 0 to 9. The example shown in FIG. 7b shows three series of numbers from 0 to 9, distributed over said periphery. The bottom face of said disk includes said first and second peripheral sets of teeth 118, 111, as visible in FIG. 7a. Preferably, the first set of teeth 118 is radially inside the second set of teeth 111, the teeth of the first set of teeth 118 being oriented axially, while the teeth of the second set of teeth are oriented radially outwards. The first set of teeth 118 and the two flexible tabs 131, 132 also form non-return means, preventing the first counter element 110 from turning in the opposite direction to the direction imparted thereto by the actuator member 130. As visible in FIG. 7b, the top face of said first counter element 110 may include a central portion 113 that surrounds the central opening 115 and that is extended radially outwards by an intermediate portion 114 that is raised axially relative to said central portion 113. Said intermediate portion 114 is thus extended radially outwards by said first peripheral edge portion 112 that is raised axially relative to said intermediate portion. This embodiment makes it possible to superpose the second counter element 120 on the first counter element with an overall thickness that is small.

Figure 8A:
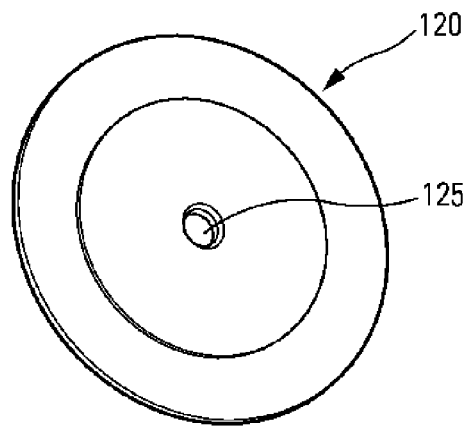
FIGS. 8a and 8b are diagrammatic front and rear views respectively of the second rotary counter element, in an advantageous variant embodiment.
Figure 8B:
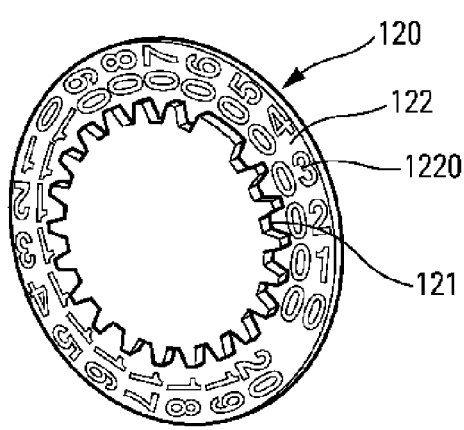

As shown in FIGS. 8a and 8b, said second counter element 120 may include a third peripheral set of teeth 121, which set is adapted, on every tenth actuation of the actuator member 130, to co-operate with said intermediate element 140. Advantageously, said second counter element is also substantially disk shaped, being provided with a central orifice 125 that, in the example shown, is blind, and that is adapted to be engaged around its pivot pin 161. The top face of said disk includes a second radially-outer peripheral edge portion 122 that receives counter indices 1220, such as the numbers from 00 to 20, distributed over said periphery. In this example, the counter is thus capable of counting 200 doses. The top face of said disk also includes said third peripheral set of teeth 121, disposed radially inside said second outer peripheral edge portion 122, said third peripheral set of teeth 121 being raised axially relative to said second outer peripheral edge portion 122. Advantageously, after assembling the first and second counter elements 110, 120 around their common pivot pin 161, said second outer peripheral edge portion 122 of said second counter element 120 is disposed radially inside, and substantially in contact with, said first outer peripheral edge portion 112 of said first counter element 110, the top surfaces of said first and second peripheral edge portions 112, 122 being substantially in alignment or coplanar, so as to form the display zone that is visible through the viewing window 151.

Figure 4:
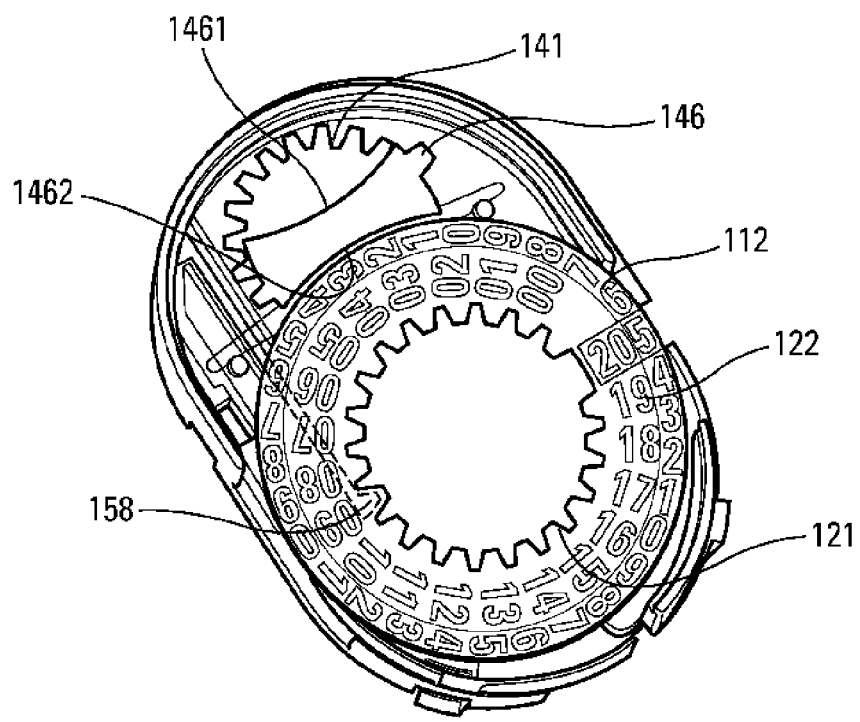
FIG. 4 is a diagrammatic perspective view partially in section of the two rotary counter elements and of the intermediate rotary element, in an advantageous embodiment of the invention, the intermediate element being in the assembled position.
Figure 9A:
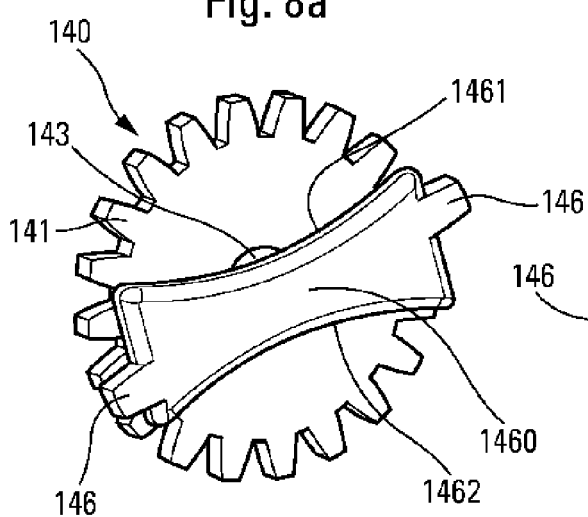
FIGS. 9a and 9b are diagrammatic front and rear views respectively of the intermediate rotary element, in an advantageous variant embodiment.
Figure 9B:
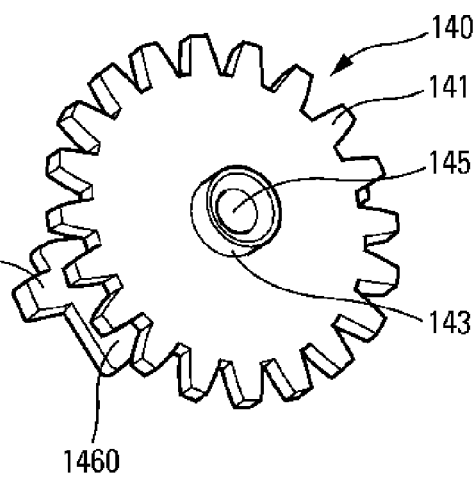

As visible in FIGS. 9a and 9b, said intermediate element 140 may include a fourth peripheral set of teeth 141, which set, on each actuation of the actuator member 130, co-operates with the second peripheral set of teeth 111 of said first counter element 110. In this way, each actuation of the dispenser device 200 is transformed, by the actuator member 130, into a turn of the first counter element 110. Advantageously, said intermediate element 140 also includes at least one radial projection 146 that, on every tenth actuation of the actuator member 130, co-operates with the third peripheral set of teeth 121 of the second counter element 120. The radial projection 146 may be formed on a radial rod portion 1460 of said intermediate element 140. Advantageously, said intermediate element 140 includes a central axial hollow sleeve 143, that, in the example shown, is blind, and that defines a central orifice 145 that is adapted to be engaged around its pivot pin 162. The fourth set of teeth 141 and said radial rod portion 1460 are offset relative to each other along said sleeve 143, defining between them a gap that may receive the first outer peripheral edge portion 112 of the first counter element 110, and the second outer peripheral edge portion 122 of the second counter element 120. Advantageously, said radial rod portion 1460 comprises two diametrally-opposite radially-outer projections 146 that are interconnected by a curved rod zone having side edges that are in the shape of circular arcs facing in substantially opposite directions, as clearly visible in FIGS. 4 and 9a. Thus, in an appropriate orientation, shown in FIG. 4, the first and second counter elements 110, 120 may be assembled one after the other on their common pivot pin 161, after the intermediate element 140 has been assembled on its own pivot pin 162. The present invention thus makes it possible to avoid two rotary elements of the counter needing to be assembled simultaneously around two offset pivot pins, as generally occurs with counters of this type.

Advantageously, said actuator member 130 is assembled in said base body 160. The lid 150 may include a flexible tab 158, visible in FIG. 4, that co-operates with the third set of teeth 121 of said second counter element 120, so as to prevent said second counter element 120 from turning in either direction when the intermediate element 140 is not co-operating with said second counter element 120. Naturally, said flexible tab 158 may deform resiliently so as to make it possible for said second counter element 120 to turn each time said intermediate element 140 co-operates with said second counter element 120, i.e. on every tenth actuation of said actuator member 130. Advantageously, abutment means are provided so as to form an abutment against axial movement of the flexible tabs 131, 132. The abutment means may advantageously be formed by the first projection 161 of the base body 160 that may co-operate with a window 136 of the actuator member 130. Other abutment means could also be envisaged. Each of the tabs 131 and 132 supports a respective lug 1310 and 1320 that co-operates with the first set of teeth 118 of the first counter element 110. The shapes of the lugs 1310 and 1320 are inverted such that the first lug 1310 pushes a tooth of the set of teeth 118 while the reservoir is descending in the body 201, and such that the second lug 1320 pulls a tooth while the reservoir is rising in the body 201. Advantageously, the flexible tabs 131 and 132 are substantially rigid axially and are flexible in a direction that is perpendicular to the axial movement of the actuator member 130. This enables the resilient tab, that does not act to turn the first counter element 110, to deform so as to slide over the set of teeth and engage in the next tooth. The two resilient tabs 131 and 132 also form the non-return means for the first counter element 110. Advantageously, the actuator member 130 includes resilient means 169, such as two resilient blades that co-operate with two appropriate shoulders 168 of the base body 160, so as to form a return spring for the actuator member 130. Preferably, the actuator member 130 further includes an axially deformable portion 134 that supports the actuator element 135. This makes it possible to continue the axial movement of the actuator element 135 (and thus of the reservoir) after the abutment position defined by the projection 161 and by the window 136 has been reached. The abutment may be formed such that a turn through exactly half a tooth is obtained while the reservoir is descending (when the first lug pushes the set of teeth 118), and such that the turn through the remaining half a tooth is obtained while the reservoir, and thus the actuator member 130, is rising under the effect of the resilient means 169 (when the second lug pulls on the set of teeth 118). Since the actuation of the valve generally requires a greater stroke, and thus a greater axial movement of the reservoir, the deformable portion 134 of the actuator member 130 makes it possible to continue the axial movement of the reservoir to its full stroke. In addition, the system makes it possible to actuate the counter before beginning to dispense the fluid.

In particular, the present invention makes it possible to simplify substantially the method of assembling a counter. Thus, the actuator member 130 is firstly assembled in said base body 160, with the actuator element 135 extending out from said base body 160 through said opening 165. Then, the intermediate rotary element 140 is assembled on its projection 162 of said base body. After appropriate orientation of said intermediate element in the assembled position shown in FIG. 4, the first rotary counter element 110 and then the second rotary counter element 120 may be assembled on their projection 161. Finally, the lid 150 may be assembled on said base body 160, so as to form a pre-assembled counter unit.

The counter of the invention also presents the advantage of being very thin, thereby enabling the outside dimensions of the device to be reduced, and the handling of the device to remain substantially unmodified. Typically, the thickness of the pre-assembled counter may be less than 7 mm, advantageously less than 6 mm, possibly even less than 5 mm.

In advantageous manner, the counter is actuated in two stages, a first stage prior to dispensing the fluid through the dispenser orifice 203 of the body 201, and a second stage after the fluid has been dispensed. Advantageously, the counter does not operate while the fluid is actually being dispensed, and its safe and reliable operation is thus completely independent of the way in which the user actuates the device in order to dispense fluid.

Naturally, compared with the above description, the counter could be made in a manner that is different from the manner shown. In particular, the shapes and positions of the first and second flexible tabs 131 and 132 could be different. It could also be envisaged to invert the functions of the first and second flexible tabs 131, 132, i.e. the first flexible tab 131 could pull the first counter element 110, while the second flexible tab 132 could push it. In addition, the shape of the deformable portion 134 that supports the actuator element 135 could be different from the shape shown in FIG. 3.

Other modifications may also be envisaged by a person skilled in the art, without going beyond the ambit of the present invention, as defined by the accompanying claims.

The invention claimed is:

1. A dose counter (100) for counting the number of doses of fluid or powder that have been dispensed or that remain to be dispensed from a fluid dispenser device (200), said counter including a first rotary counter element (110) forming a units wheel, and a second rotary counter element (120) forming a tens wheel, said first and second counter elements (110; 120) co-operating with each other to define and to display, in a viewing window (151), said number of doses, said first counter element (110) co-operating with an actuator member (130) that is adapted to cause said first counter element (110) to turn each time said actuator member (130) is actuated, said counter including an intermediate rotary element (140) that is adapted to cause said second counter element (120) to turn on every tenth actuation of said actuator member (130), said first and second counter elements (110; 120) turn about a common first pivot pin (161), and said intermediate element (140) turns about a second pivot pin (162) that is offset and parallel to said first pivot pin (161), said counter being characterized in that said first counter element (110) includes: a first peripheral set of teeth (118), which set, on each actuation, co-operates with at least one actuator tab (131, 132) of the actuator member (130); and a second peripheral set of teeth (111), which set, on each actuation, co-operates with said intermediate element (140), said second counter element (120) includes a third peripheral set of teeth (121), which set, on every tenth actuation of the actuator member (130), co-operates with said intermediate element (140).

2. A counter according to claim 1, wherein said first set of teeth (118) is radially inside the second set of teeth (111), the teeth of the first set of teeth (118) being oriented axially, and the teeth of the second set of teeth (118) being oriented radially outwards.

3. A counter according to claim 1, wherein said first counter element (110) is substantially in the shape of a disk provided with a central through opening (115) that is adapted to be engaged around its pivot pin (161), the top face of said disk including a first radially-outer peripheral edge portion (112) that receives counter indices (1120), such as one or more series of numbers from 0 to 9, in particular three series of numbers from 0 to 9, distributed over said periphery, and the bottom face of said disk including said first and second peripheral sets of teeth (118, 111).

4. A counter according to claim 3, wherein the top face of said first counter element (110) includes a central portion (113) that surrounds the central opening (115) and that is extended radially outwards by an intermediate portion (114) that is raised axially relative to said central portion, said intermediate portion (114) being extended radially outwards by said first peripheral edge portion (112) that is raised axially relative to said intermediate portion (114).

5. A counter according to claim 1, wherein said second counter element (120) is substantially in the shape of a disk provided with a central orifice (125), in particular a blind orifice, that is adapted to be engaged around its pivot pin (161), the top face of said disk including a second radially-outer peripheral edge portion (122) that receives counter indices (1220), such as numbers from 00 to 20, distributed over said periphery, the top face of said disk also including said third peripheral set of teeth (121), disposed radially inside said second outer peripheral edge portion (122), said third peripheral set of teeth (121) being raised axially relative to said second outer peripheral edge portion (122).

6. A counter according to claim 3, wherein after assembling the first and second counter elements (110; 120) around their common pivot pin (161), said second outer peripheral edge portion (122) of said second counter element (120) is disposed radially inside, and substantially in contact with, said first outer peripheral edge portion (112) of said first counter element (110), the top surfaces of said first and second peripheral edge portions (112; 122) being substantially in alignment, so as to form a display zone.

7. A counter according to claim 1, wherein said intermediate element (140) includes a fourth peripheral set of teeth (141), which set, on each actuation of the actuator member (130), co-operates with a second peripheral set of teeth (111) of said first counter element (110).

8. A counter according to claim 1, wherein said intermediate element (140) includes at least one radial projection (146) that, on every tenth actuation of the actuator member (130), co-operates with a third peripheral set of teeth (121) of the second counter element (120).

9. A counter according to claim 8, wherein said at least one radial projection (146) is formed on a radial rod portion (1460) of said intermediate element (140).

10. A counter according to claim 9, wherein said intermediate element (140) includes a central axial hollow sleeve (143), in particular a blind hollow sleeve, that defines a central orifice (145) that is adapted to be engaged around its pivot pin (162), said fourth set of teeth (141) and said radial rod portion (1460) being offset relative to each other along said sleeve (143), defining between them a gap for receiving a first outer peripheral edge portion (112) of the first counter element (110), and a second outer peripheral edge portion (122) of the second counter element (120).

11. A counter according to claim 10, wherein said radial rod portion (1460) comprises two diametrally-opposite radially-outer projections (146) that are interconnected by a curved rod zone having side edges (1461; 1462) that are in the shape of circular arcs facing in substantially opposite directions, such that in an appropriate orientation, the first and second counter elements (110; 120) may be assembled on their common pivot pin (161), after the intermediate element (140) has been assembled on its own pivot pin (162).

12. A counter according to claim 1, wherein the counter includes a base body (160) and a lid (150), said base body (160) incorporating the two pivot pins (161, 162) and an opening (165), and said lid (150) incorporating a viewing window (151).

13. A counter according to claim 12, wherein said counter may be pre-assembled so as to form a counter unit, said counter unit including fastener means for fastening to a body (201) of a fluid dispenser device (200).

14. A counter according to claim 12, wherein said actuator member (130) is assembled in said base body (160), said actuator member (130) including an actuator element (135)

that is movable in translation in said opening (165), and two flexible tabs (131, 132) that are movable in translation, a first flexible tab (131) co-operating with said first set of teeth (118) of the first counter element (110) so as to cause said first counter element (110) to turn in a counting direction each time the actuator element (135) is moved from a rest position to an actuated position, and a second flexible tab (132) co-operating with said first set of teeth (118) of said first counter element (110) so as to cause said first counter element (110) to turn in the same counting direction when the actuator element (135) returns from its actuated position to its rest position.

15. A counter according to claim 14, wherein, on each actuation, the first flexible tab (131) pushes a respective first tooth of the first set of teeth (118) of the first counter element (110), and the second flexible tab (132) pulls on a respective second tooth of the first set of teeth (118) of said first counter element (110).

16. A counter according to claim 15, wherein the first and second teeth of the first set of teeth (118) are substantially diametrally opposite in the first set of teeth (118).

17. A counter according to claim 14, wherein the actuator member (130) includes an elongate opening (136) that is engaged around a projection (161) of said base body (160), the co-operation between said projection (161) and the edges of said elongate opening (136), while the actuator member (130) is being actuated, defining the limits of the axial movement of said flexible tabs (131, 132).

18. A counter according to claim 17, wherein the actuator member (130) includes an elastically-deformable portion (134) that supports the actuator element (135), such that said actuator element (135) is movable in translation over a greater distance than the flexible tabs (131, 132).

19. A counter according to claim 12, wherein said base body (160) includes two shoulders (168) that co-operate with two resilient means (169) of the actuator member (130), said resilient means (169) forming a return spring for the actuator member (130).

20. A counter according to claim 12, wherein said lid (150) includes a flexible tab (158) that co-operates with a third set of teeth (121) of said second counter element (120), so as to prevent said second counter element (120) from turning while the actuator member (130) is being actuated, the intermediate element (140) not co-operating with said second counter element (120), said flexible tab (158) deforming resiliently so as to make it possible for said second counter element (120) to turn when said intermediate element co-operates with said second counter element, on every tenth actuation of said actuator member (130).

21. A fluid or powder dispenser device (200) comprising a reservoir, a dispenser member, such as a metering valve, that is mounted on said reservoir, and a body (201) incorporating a dispenser orifice (203), said reservoir being movable in said body (201) so as to dispense the fluid or powder, said dispenser device (200) being characterized in that it includes a counter (100) according to claim 1.

22. A device according to claim 21, wherein said counter (100) is fastened on a face of the body (201), said device being actuated by the user pressing axially on the reservoir, and said counter being actuated by said axial movement of said reservoir that co-operates with said actuator element (135) of the actuator member (130).

23. A method of assembling a counter (100) according to claim 1, said method being characterized in that it comprises the following steps:
   providing a base body (160) that is provided with two parallel projections (161, 162) and with an opening (165);
   assembling an actuator member (130) in said base body (160), said actuator member (130) including an actuator element (135) that extends out from said base body (160) through said opening (165) of the base body;
   assembling an intermediate rotary element (140) on a first (162) of said two projections (161, 162) of said base body (160);
   assembling a first rotary counter element (110) on a second (161) of said two projections (161, 162) of said base body (160);
   assembling a second rotary counter element (120) on said second projection (161) of said base body (160); and
   assembling a lid (150) on said base body (160), so as to form a pre-assembled counter unit.

\* \* \* \* \*